United States Patent [19]

DeLue

[11] 4,404,398

[45] Sep. 13, 1983

[54] PREPARATION OF UNSATURATED FLUOROCARBON ACIDS

[75] Inventor: Norman R. DeLue, Corpus Christi, Tex.

[73] Assignee: PPG Industries, Inc., Pittsburgh, Pa.

[21] Appl. No.: 324,747

[22] Filed: Nov. 25, 1981

Related U.S. Application Data

[63] Continuation of Ser. No. 868,787, Jan. 12, 1978.

[51] Int. Cl.$^3$ .............................................. C07C 57/04
[52] U.S. Cl. .................................. 562/598; 562/600; 562/586; 562/551
[58] Field of Search ............................... 562/598, 600

[56] References Cited

U.S. PATENT DOCUMENTS 3,309,348  3/1967  Wentz .................................. 562/551
3,529,018  9/1970  Andersson ........................... 562/551

FOREIGN PATENT DOCUMENTS 571473   4/1975  U.S.S.R. ............................... 562/598
614089  11/1975  U.S.S.R. ............................... 562/598

OTHER PUBLICATIONS

Pfeffer, P. et al., J. Organic Chem. 36 3290 (1971).
Lassar-Cohn, Laboratory Manual of Organic Chemistry, p. 336 Mar., Advanced Organic Chemistry: Reactions, Mechanisms & Structure.
D. Seyforth, "The Preparation of Organolithium Compounds by the Transmetalation Reaction, V-Perfluorovinyllithium", J. Am. Chem. Soc. 84, 4266-4269.

Primary Examiner—Paul J. Killos
Attorney, Agent, or Firm—Richard M. Goldman

[57] ABSTRACT

Disclosed is a method of preparing alpha-beta and beta-gamma unsaturated monocarboxylic acids having electron withdrawing, electrophilic substituents at the site of unsaturation. The acids are prepared by reacting metal salts of the unsaturated acids with strong mineral acids under substantially anhydrous conditions.

7 Claims, No Drawings

PREPARATION OF UNSATURATED FLUOROCARBON ACIDS

This is a continuation of application Ser. No. 868,787, filed Jan. 12, 1978.

DESCRIPTION OF THE INVENTION

Fluorinated unsaturated carboxylic acids, especially perfluorinated unsaturated carboxylic acids find utility in the preparation of ion exchange membranes, permionic membranes, and solid electrolytes. The ion exchange membranes, permionic membranes, and solid electrolytes prepared therefrom are useful in carrying out chemical processes where properties such as electrical conductivity and controlled water permeability within a specified narrow range must be combined with extreme chemical resistance to such materials as nascent chlorine, strong acids, and strong alkalis.

One process where these properties are necessary is the electrolysis of alkali metal chlorides, such as sodium chloride or potassium chloride, in an electrolytic cell to yield an anode product of chlorine and a cathode product of alkali metal hydroxide, e.g., sodium hydroxide or potassium hydroxide. In the electrolytic production of chlorine and an alkali metal hydroxide, a strongly acidic anolyte liquor must be kept separate from a strongly basic catholyte liquor in order to provide high electrical current efficiency. Moreover, cations, e.g., alkali metals such as sodium ions or potassium ions must be allowed to pass through the barrier interposed between the anolyte liquor and the catholyte liquor.

This has been accomplished in the past by imposing a fluid permeable barrier between the anolyte liquor and the catholyte liquor, for example, a fluid permeable diaphragm of chrysotile asbestos. More recently, this has been accomplished by providing an electrolyte impermeable but cation permeable permionic membrane, that is, a cation selective permionic membrane, between the anolyte liquor and the catholyte liquor. Such cation selective permionic membranes have typically been provided by a perfluorocarbon polymer having pendant sulfonyl groups, for example, sulfonic acid groups, sulfonyl halide groups, or alkali metal sulfonyl salt groups.

More recently, it has been found that a particularly desirable permionic membrane, that is, a particularly desirable membrane substantially impermeable to the bulk or hydraulic flow of the electrolyte but permeable to the flow of cations through the membrane, i.e., the flow of alkali metal ions through the membrane, may be provided by a membrane having pendant carboxylic acid groups on a perfluorinated polymer backbone.

Such membranes may be provided by the reaction product of a perfluorinated acid moiety with a halogenated alkene, for example, with tetrafluoroethylene, trifluoroethylene, chlorotrifluoroethylene, vinylidene fluoride, vinyl fluoride, hexafluoropropylene, and copolymers of hexafluoropropylene or perfluoroethylene with perfluorinated alkoxy compounds. The acid moiety may be a perfluoroacrylic acid, perfluoromethacrylic acid, or a fluorinated unsaturated acid being suitably chain extended, for example, by the reaction with a perfluorinated epoxy compound whereby to provide ether linkages between the terminal acid group and the backbone of the polymer.

The synthesis of perfluoroacrylic acid or perfluoromethacrylic acid useful in providing the acid moiety or in providing a terminal element of the acid moiety, typically involves the synthesis of a metal salt of the unsaturated perfluoro acid followed by acidification and formation of the free acid. In the prior art, the acidification has been carried out by reaction with a strong aqueous acid. When the acidification is carried out in aqueous media, for example, in aqueous hydrochloric acid or aqueous sulfuric acid, it is found that the yield of fluorinated, unsaturated acid is low. The overall yield for the synthesis of the unsaturated, perfluorinated acid is typically on the order of from about 30 to about 40 percent.

It has now been found that the yield of the fluorinated, unsaturated monocarboxylic acid may be increased significantly, for example, to in excess of 70 percent, by acidification of the metal salt of the unsaturated, fluorinated acid in substantially anhydrous media.

DETAILED DESCRIPTION OF THE INVENTION

Disclosed is a method of preparing unsaturated, organic, monocarboxylic acids. The unsaturated carboxylic acids herein contemplated have either alpha-beta unsaturation or beta-gamma unsaturation and have electrophilic substituents on the unsaturated carbon atoms. According to the method herein contemplated, a metal salt of the unsaturated organic monocarboxylic acid is reacted with a strong acid, that is, an acid stronger than the unsaturated organic carboxylic acid, under substantially anhydrous conditions, whereby to form the fluorinated unsaturated organic monocarboxylic acid. The strong acid is normally a mineral acid chosen from the group consisting of anhydrous hydrogen chloride, anhydrous hydrogen bromide, and anhydrous sulfuric acid. However, tri-halo acetic acids, e.g., trichloroacetic acid or trifluoroacetic acid, may also be used with satisfactory results. Most commonly, the strong mineral acid is anhydrous hydrogen chloride. According to a preferred exemplification of the method of this invention, the anhydrous hydrogen chloride is gaseous.

The metal salt of the unsaturated organic carboxylic acid is normally an alkali metal salt or an alkaline earth metal salt. When the salt is an alkali metal salt, it is most frequently a lithium or sodium salt and preferably a lithium salt. When the salt is an alkaline earth metal salt, it is most frequently a magnesium salt prepared by a Grignard reaction.

The unsaturated, organic monocarboxylic acid herein contemplated is chosen from the group consisting of organic carboxylic acids having the formula:

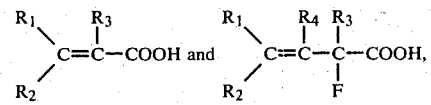

where $R_1$, $R_2$, $R_3$ and $R_4$ are electrophilic substituents chosen from the group consisting of F, Cl, H, $(CF_2)_nCF_3$ and $O(CF_2)_nCF_3$ where n is a number from 0 to 9. At least one of the substituents $R_1$, $R_2$, and $R_3$ is a fluorine atom.

According to one exemplification, the unsaturated organic acids prepared by the method of this invention have $\alpha$-$\beta$ unsaturation and a general formula of the type:

$$\begin{array}{c}R_1\\ \\R_2\end{array}\!\!\!\!C\!\!=\!\!\begin{array}{c}R_3\\|\\C\!\!-\!\!COOH\end{array}$$

where $R_1$, $R_2$, and $R_3$ are electrophilic substituents chosen from the group consisting of —F, —Cl, —H, —$(CF_2)_nCF_3$ and —$O(CF_2)_nCF_3$, where n is from 0 to 9 and at least one of the substituents is a fluorine atom. Typical organic monocarboxylic acids having α-β unsaturation and prepared by the method contemplated herein include:

$CF_2=CF—COOH$, $CFH=CF—COOH$, $CH_2=CF—COOH$, $CF_2=CH—COOH$, $CFH=CH—COOH$, $$CF_2=\underset{\underset{CF_3}{|}}{C}-COOH,$$

$$CFH=\underset{\underset{CF_3}{|}}{C}-COOH,$$

$$CH_2=\underset{\underset{CF_3}{|}}{C}-COOH,$$

$CF_3—CF=CF—COOH$, $CF_3—CH=CF—COOH$, $CF_3—CH=CH—COOH$, $CF_3—CF=CH—COOH$, $$CF_3-CF=\underset{\underset{CF_3}{|}}{C}-COOH,$$

$CF_3—O—CF=CF—COOH$, $CF_3—O—CH=CF—COOH$, $CF_3—O—CH=CH—COOH$, $CF_3—O—CF=CH—COOH$, $$CF_3-O-CF=\underset{\underset{CF_3}{|}}{C}-COOH,$$

$$CF_3-O-CH=\underset{\underset{CF_3}{|}}{C}-COOH,$$

$$CF_2=\underset{\underset{\underset{CF_3}{|}}{\underset{|}{O}}}{C}-COOH,$$

$$CFH=\underset{\underset{\underset{CF_3}{|}}{\underset{|}{O}}}{C}-COOH,$$

$$CH_2=\underset{\underset{\underset{CF_3}{|}}{\underset{|}{O}}}{C}-COOH,$$

$$CF_3-CF=\underset{\underset{\underset{CF_3}{|}}{\underset{|}{O}}}{C}-COOH,$$

$$CF_3-CH=\underset{\underset{\underset{CF_3}{|}}{\underset{|}{O}}}{C}-COOH, \text{ and}$$

$$CF_3-O-CF=\underset{\underset{\underset{CF_3}{|}}{\underset{|}{O}}}{C}-COOH.$$

While the above structures are shown with H and F, it should also be understood that both —Cl and —F substituents may be present, especially at the site of α-β unsaturation. The method of this invention is especially useful in preparing perfluorinated organic acids having α-β unsaturation, such as:

$CF_2=CF—COOH$, $$CF_2=\underset{\underset{CF_3}{|}}{C}-COOH,$$

$CF_3—CF=CF—COOH$, $$CF_3-CF=\underset{\underset{CF_3}{|}}{C}-COOH,$$

$CF_3—O—CF=CF—COOH$, $$CF_3-O-CF=\underset{\underset{CF_3}{|}}{C}-COOH,$$

$$CF_3-O-CF=\underset{\underset{\underset{CF_3}{|}}{\underset{|}{O}}}{C}-COOH, \text{ and}$$

$$CF_3-CF=\underset{\underset{\underset{CF_3}{|}}{\underset{|}{O}}}{C}-COOH.$$

The method of this invention is especially useful in preparing perfluoroacrylic acid, perfluoromethacrylic acid, and perfluorocrotonic acid, $CF_2=CF—COOH$, CF₂=C—COOH, and
    |
    CF₃

CF₃—CF=CF—COOH.

According to an alternative exemplification, the unsaturated organic acids prepared by the method of this invention have β-γ unsaturation and a general formula of the type:

$$R_1 \atop R_2 \diagdown C=C-C-COOH \atop \diagup \; R_4 \; R_3 \atop F$$

where $R_1$, $R_2$, $R_3$, and $R_4$ are electrophilic substituents chosen from the group consisting of —F, —Cl, —H, —(CF₂)ₙCF₃, and —O(CF₂)ₙCF₃, where n is from 0 to 9 and at least one of the substituents $R_1$, $R_2$, $R_3$, and $R_4$ is a fluorine atom. Typical organic monocarboxylic acids having β-γ unsaturation and prepared by the method contemplated herein include:

CF₂=CF—CF₂—COOH,

CFH=CF—CF₂—COOH,

CH₂=CF—CF₂—COOH,

CH₂=CH—CF₂—COOH,

CF₂=CF—CHF—COOH,

CF₂=CF—CH₂—COOH,

CF₂=CH—CH₂—COOH,

CFH=CH—CH₂—COOH,

CF₂=CH—CF₂—COOH,

CF₂=CH—CHF—COOH,

CF₃—O—CF=CF—CF₂—COOH,

CF₃—O—CH=CF—CF₂—COOH,

CF₃—O—CH=CH—CF₂—COOH,

CF₃—O—CH=CH—CHF—COOH,

CF₃—O—CF=CH—CF₂—COOH,

CF₃—O—CF=CH—CHF—COOH,

CF₂=C—CF₂—COOH,
    |
    O
    |
    CF₃

CFH=C—CF₂—COOH,
    |
    O
    |
    CF₃

CH₂=C—CF₂—COOH,
    |
    O
    |
    CF₃

CF₂=C—CFH—COOH,
    |
    O
    |
    CF₃

CF₂=C—CH₂—COOH,
    |
    O
    |
    CF₃

CFH=C—CFH—COOH,
    |
    O
    |
    CF₃

CFH=C—CH₂—COOH,
    |
    O
    |
    CF₃

CF₂=CF—CF—COOH,
       |
       O
       |
       CF₃

CFH=CF—CF—COOH,
       |
       O
       |
       CF₃

CFH=CH—CF—COOH,
       |
       O
       |
       CF₃

CF₃CF=CF—CF₂—COOH,

CF₃CH=CF—CF₂—COOH,

CF₃CH=CF—CFH—COOH,

CF₃CF=CH—CF₂—COOH,

CF₃CF=CH—CFH—COOH,

CF₂=C—CF₂—CF₂—COOH,
    |
    CF₃

CFH=C—CF₂—CF₂—COOH,
    |
    CF₃

CFH=C—CFH—CF₂—COOH,
    |
    CF₃

CFH=C—CH₂—CF₂—COOH,
    |
    CF₃

CFH=C—CFH—CFH—COOH,
    |
    CF₃

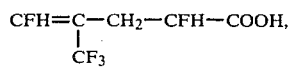

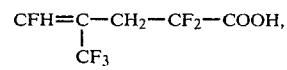

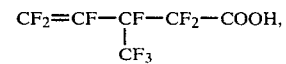

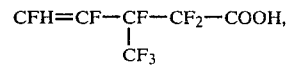

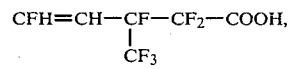

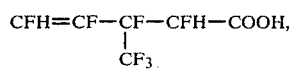

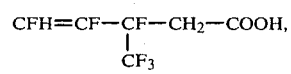

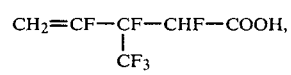

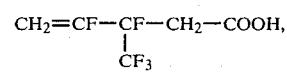

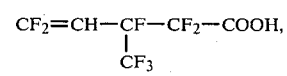

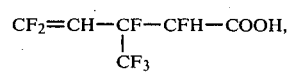

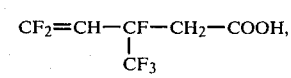

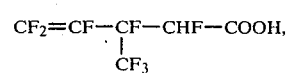

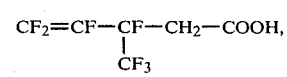

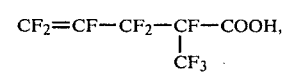

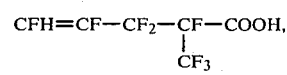

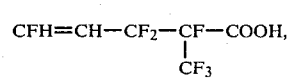

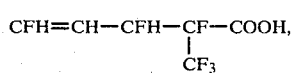

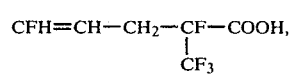

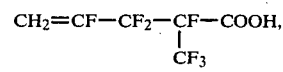

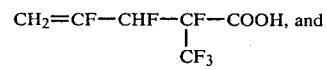

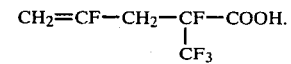

While the above structures are shown with H and F, it should also be understood that both —Cl and —F substituents may be present, especially at the site of β-γ unsaturation.

The method of this invention is especially useful in preparing perfluorinated organic acids having β-γ unsaturation, such as:

$CF_2=CF-CF_2-COOH,$ $CF_3-O-CF=CF-CF_2-COOH,$

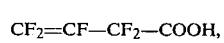

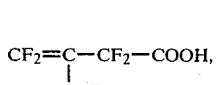

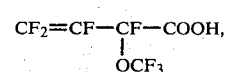

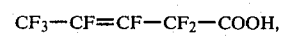

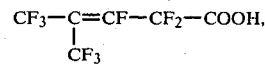

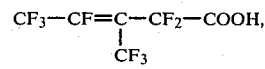

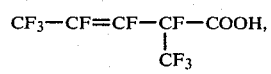

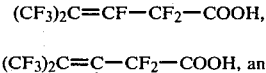

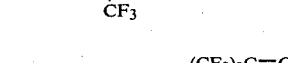

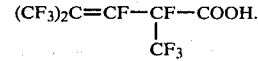

The method of this invention is especially useful in synthesizing perfluoro acids having β-γ unsaturation and having the structural formula:

$CF_2=CF-CF_2-COOH.$

According to the method of this invention, unsaturated fluorocarbon monocarboxylic acids having alpha-beta unsaturation and unsaturated fluorocarbon monocarboxylic acids having beta-gamma unsaturation may be prepared. By a monocarboxylic acid is meant an organic acid having a single COOH or a derivative thereof as a terminal group. By a derivative of a —COOH group is meant a terminal group chosen from —COOH, —CN, —COF, —COOR$_5$, —COOMe, and CONR$_6$R$_7$, where R$_5$ is a C-1 to C-10 alkyl group and preferably a C-1 to C-3 alkyl group, R$_6$ and R$_7$ may either be hydrogen atom or a C-1 to C-10 alkyl group, and Me represents either an alkali metal or a quaternary ammonium group. By alpha-beta unsaturation is meant unsaturation of the type represented by the structure

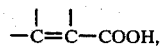

while by beta-gamma unsaturation is meant the type of unsaturation represented by the structural formula

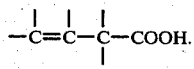

The method of this invention results in significantly increasing the yield of unsaturated fluorocarbon carboxylic acids by acidification of the metal salt of the acid under substantially anhydrous conditions.

According to one exemplification of this invention, the metal salt is an alkali metal salt having the formula —C=C—COOM, where M represents an alkali metal. The alkali metal may be either sodium or lithium. Most frequently, for ease in synthesis of the intermediates, the alkali metal is lithium. According to one exemplification of this invention, a tri-substituted ethylene having the structural formula:

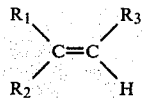

where the R's are electrophilic substituents and at least one of the R's is fluorine reacted with an alkyl derivative of an alkali metal, for example, n-butyl lithium whereby to form an organometallic compound having the structural formula:

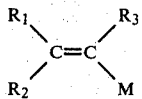

where M is an alkali metal and the corresponding alkane, e.g., butane. Thereafter, the organometallic compound is reacted with carbon dioxide to form the carboxylic acid salt of the alkali metal by the reaction:

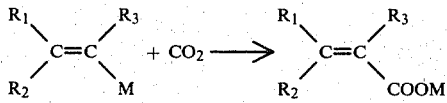

When the reaction sequence described above for producing the alkali metal salt of the fluorinated unsaturated carboxylic acid is utilized, most frequently the alkane is n-butane and most frequently the alkali metal is lithium, although it may also be sodium.

n-Butyl lithium can be produced by reacting an n-butyl halide, for example, n-butyl chloride or n-butyl bromide, with lithium containing from about 0.02 to about 2 weight percent sodium in a suitable solvent such as ether, benzene, cyclohexane, or the like. n-Butyl sodium, and alkyl sodiums generally, can be prepared by reacting the alkyl halides such as an alkyl chloride or alkyl bromide with finely divided sodium. By finely divided sodium is meant sodium metal having a size from about 10 to about 30 microns in a suitable solvent.

The alkyl compound of the alkali metal is then reacted with the tri-substituted ethylene in an organic solvent such as ether, hexane, cyclohexane, benzene, or the like. The reaction is carried out below the boiling points of the reagents, solvents, and products, e.g., below about 0° C. This may be accomplished by carrying out the reaction in a cooling bath of solid carbon dioxide in acetone, providing a reaction temperature of $-78°$ C. The reaction is normally carried substantially to completion, i.e., for about 30 minutes to one hour.

Thereafter, the reaction medium, i.e., the solvent such as hexane, ether, or the like, and the reaction product of the tri-substituted ethylene with the alkali metal compound of the alkyl is contacted with carbon dioxide. Gaseous carbon dioxide may be bubbled through the reaction medium or the reaction medium may be contacted with solid carbon dioxide. According to a preferred exemplification, the carbon dioxide is solid carbon dioxide. The reaction medium may be poured over the solid carbon dioxide under a substantially inert atmosphere or solid carbon dioxide may be added to the reaction medium under a substantially inert atmosphere.

The reaction product of the carbon dioxide and the $R_1R_2C$=$CR_3M$ is a suspension of white solids, for example, a pasty suspension of white solids. Thereafter, the suspension of white solids in the solvent is contacted with a strong acid. By a strong acid is meant an acid that is stronger than the fluorinated, unsaturated monocarboxylic acid intended to be produced. Most commonly this acid is a mineral acid such as sulfuric acid, nitric acid, hydrochloric acid, or hydrobromic acid or a strong organic acid such as trichloroacetic acid or trifluoroacetic acid. Where the acid is a gas, the gas may be bubbled through the reaction medium. Alternatively, the gas may be bubbled through or contacted with a solvent which then contacts the reaction medium.

The reaction products are the fluorinated, unsaturated monocarboxylic acid, the inorganic salt of the alkali metal, and the strong acid. The inorganic salt may then be physically separated from the organic reaction medium, for example, by filtration, centrifugation, distillation, or the like. Thereafter, the liquids may be physically separated, e.g., by distillation, absorption, extraction, or the like, thereby to obtain the unsaturated, fluorinated, monocarboxylic acid.

According to an alternative method of forming the lithium salt, trifluorovinyl lithium may be prepared by treating triphenyl(trifluorovinyl) tin with phenyl lithium. The trifluorovinyl lithium so prepared may be reacted with carbon dioxide, as described above, to form lithium perfluoroacrylate. The lithium perfluoroacrylate may then be reacted with an anhydrous acid substantially as described above whereby to form perfluoro acrylic acid.

According to a further exemplification of this invention, a trisubstituted chloroethylene, bromoethylene, or iodoethylene may be reacted with the Grignard reagent:

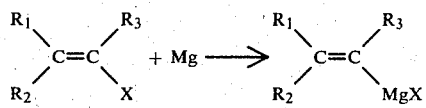

where $R_1$, $R_2$, and $R_3$ may be F, H, $(CF_2)_nCF_3$, and $O(CF_2)_nCF_3$, where n is from 0 to 9, and X is chlorine, bromine, or iodine. If X is bromine or iodine, $R_1$, $R_2$, or $R_3$ may be chlorine. At least one of the R's must be fluorine. This reaction provides an unsaturated Grignard reaction product. This product may further be reacted with carbon dioxide

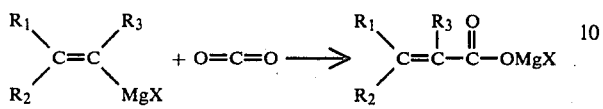

in order to provide the magnesium halide salt of the alpha-beta unsaturated Grignard reaction product. The alpha-beta unsaturated Grignard reaction product may then be contacted with substantially anhydrous acid as described hereinabove in order to form an alpha-beta unsaturated, fluorinated carboxylic acid.

In the exemplifications of this invention, where the Grignard reaction is utilized, a Grignard reagent is reacted with a substituted, unsaturated compound having a reactive halogen thereon. By reactive halogen is meant a chlorine atom, a bromine atom, or an iodine atom. Preferably, the reactive halogen is an iodine atom which is more easily removed by the Gregnard reagent than a bromine or chlorine atom. Alternatively, it may be a bromine atom which is more easily removed than a chlorine atom, or the reactive halogen can be a chlorine atom.

According to an alternative exemplification of this invention, a $\beta$-$\gamma$ unsaturated acid is produced by first reacting a $\beta$-$\gamma$ unsaturated compound having a reactive halogen with a Grignard reagent. The reaction takes place according to the reaction sequence:

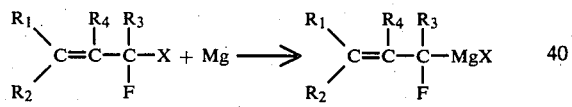

where $R_1$, $R_2$, $R_3$, and $R_4$ may be F, Cl, H, $(CF_2)_nCF_3$, and $O(CF_2)_nCF_3$ where n is from 0 to 9, at least one of the R's is a fluorine atom, and X is either iodine, bromine, or chlorine.

The Grignard reaction product is contacted with carbon dioxide, for example, by pouring the Grignard reaction product over dry ice under a suitable nonreactive atmosphere, where the reaction:

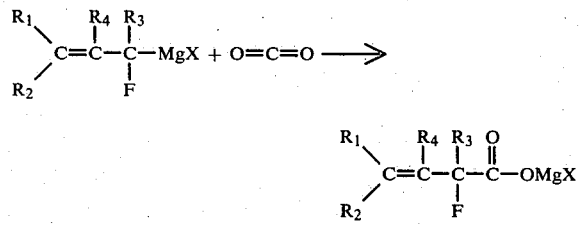

takes place.

Thereafter, the intermediate magnesium halide salt of the fluorinated organic acid, having beta-gamma unsaturation, is contacted with a substantially anhydrous acid under substantially anhydrous conditions as defined above whereby to provide the fluorinated, unsaturated, monocarboxylic organic acid according to the following reaction:

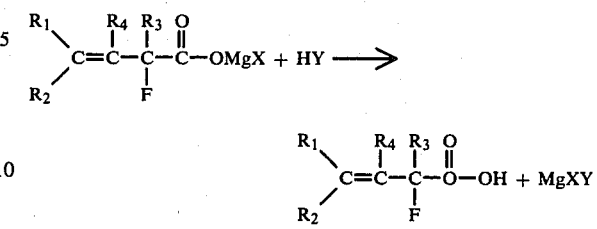

where Y is an anion group, for example, chlorine, bromine, or sulfate. X and Y may be the same anions although it is not necessary that they be the same anions.

Regardless of the method of forming the salt of the fluorinated, unsaturated, carboxylic acid, the reaction of the salt of the fluorinated, unsaturated, monocarboxylic acid, whether $\alpha$-$\beta$ unsaturated or $\beta$-$\gamma$ unsaturated, with the stronger acid is carried out under substantially anhydrous conditions. That is, the reaction is carried out under such conditions as to avoid attack of the site of unsaturation by water or by hydrogen ions or hydroxyl ions.

The reaction may be carried out by bubbling a gas of the acid through the organic reaction medium. Alternatively, a substantially anhydrous liquid, such as sulfuric acid may be added directly to the reaction medium. According to a still further exemplification, the acid may be bubbled through still another organic solvent, for example, hydrochloric acid may be bubbled through hexane or absolute ether or the like and thereafter the organic reaction medium is contacted with the organic solvent which has been treated with the acid.

The inorganic salt, i.e., the salt of the metal and the anion of the strong acid, e.g., the lithium chloride or lithium bromide, sodium chloride, sodium bromide, lithium sulfate, sodium sulfate, lithium nitrate, sodium nitrate, magnesium chloride, magnesium bromide, or magnesium iodide, is then physically separated from the organic reaction medium. This may be accomplished by filtration or by centrifugation.

Thereafter, the reaction medium may then be physically separated from the product. For example, where the solvents are ether or hexane, they may be stripped by aspiration leaving a residue. This residue may then be physically purified, e.g., sublimated, distilled, or recrystallized, in order to obtain the substantially pure unsaturated, fluorinated carboxylic acid.

According to one exemplification of this invention, perfluoroacrylic acid is prepared by first reacting trifluoroethylene with n-butyl lithium to form $CF_2=CFLi$. This is accomplished by condensing trifluoroethylene at a low temperature, for example, at $-78°$ C., the melting point of carbon dioxide, in a dry container, and adding the condensate to diethyl ether. At the same time, a liquid composition of n-butyl lithium in absolute ether is prepared and mixed with hexane. The n-butyl lithium in the hexane and absolute ether is transferred to the container containing the trifluoroethylene in absolute ether and mixed therewith in order to provide contact for a long enough period of time to allow the reaction to go to completion.

Thereafter, the $CF_2=CFLi$ formed thereby is reacted with carbon dioxide to form $CF_2=CFCOOLi$. This can be accomplished by pouring solid carbon dioxide into the reaction medium of $CF_2=CFLi$ in hexane and ether or pouring the reaction medium of hexane, ether, and $CF_2=CFLi$ over solid carbon dioxide under a suitable inert atmosphere, e.g., a nitrogen or $CO_2$ atmosphere. A pasty suspension of white solids is obtained.

A substantially anhydrous acid, for example, a gaseous hydrogen chloride, is bubbled through the reaction medium forming a white precipitate of lithium chloride. According to an alternative procedure for carrying out the method of this invention, a hydrogen chloride solution may be prepared by bubbling substantially anhydrous hydrogen chloride through a suitable organic solvent such as absolute ether or hexane. The hydrogen chloride solution prepared this way may then be added to the pasty solution of the white solids, thereby forming a white precipitate of the lithium chloride.

This slurry is then separated by physical separation, e.g., filtration. The filtrate liquid is concentrated by distillation and stripping, leaving a residue. This residue is sublimated and crystallized whereby to yield perfluoroacrylic acid, $CF_2=CFCOOH$.

According to a still further exemplification of this reaction, a solution of $CF_2=CF-CF_2Br$ in absolute diethyl ether is prepared. Under a suitable nonreactive atmosphere, e.g., nitrogen, magnesium turnings are added to the solution thereby forming a Grignard reaction product, $CF_2=CF-CF_2Br + Mg \rightarrow CF_2=CF-CF_2MgBr$. Thereafter, the reaction medium of $CF_2=CF-CF_2MgBr$ in absolute diethyl ether is added to solid carbon dioxide where the reaction:

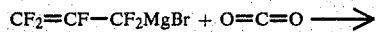

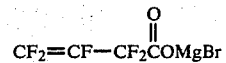

takes place. Thereafter, the resulting magnesium bromide salt of the carboxylic acid is contacted with dry hydrobromic acid gas, e.g., by bubbling HBr gas through the reaction medium whereby to form magnesium dibromide and a perfluoro 3-butenoic acid according to the reaction:

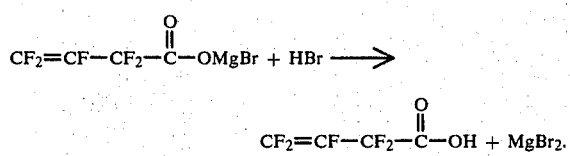

Particularly preferred unsaturated, perfluorinated, monocarboxylic acids prepared according to the method of this invention are:

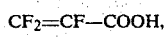

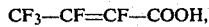

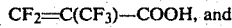

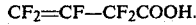

The unsaturated fluorocarbon acids prepared according to the method of this invention may be reacted further, for example, to yield chemically-resistant polymers useful in fabricating permionic membranes, ion exchange membranes, and other chemically inert materials having acidic active sites. Such further reactions may include homopolymerization, for example, free radical initiated homopolymerization. Alternatively, such further reactions may include copolymerization with unsaturated perfluorocarbon monomers, e.g., copolymerization with perfluoropropylene, with tetrafluoroethylene, or with copolymers of perfluoropropylene and tetrafluoroethylene. Normally such copolymerizations are free radical initiated polymerizations and they may be emulsion polymerizations or suspension polymerizations. Alternatively, such copolymerizations may be graft copolymerizations.

According to an alternative exemplification, the acids prepared according to the method of this invention may be copolymerized with partially fluorinated compounds such as vinyl fluoride, vinylidene fluoride, and chlorotrifluoroethylene or with perfluoro alkoxys.

According to a still further exemplification, the unsaturated acids produced by the method of this invention can be reacted with an epoxide, e.g., perfluoroethylene oxide,

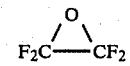

whereby to yield a prepolymer having the structural representation,

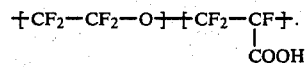

EXAMPLE

Perfluoroacrylic acid was prepared by reacting trifluoroethylene with n-butyl lithium to form $CF_2=CFLi$. The $CF_2=CFLi$ was then reacted with carbon dioxide to form $CF_2=CFCOOLi$, which was reacted with dry, gaseous hydrogen chloride to form perfluoroacrylic acid and lithium chloride.

Trifluoroethylene was condensed at $-78°$ C. in a graduated centrifuge tube that had been dried and flushed with nitrogen. 5.7 grams of the condensed trifluoroethylene was then introduced into a 300 milliliter flask that contained 150 milliliters of absolute ether. The flask was cooled in a dry ice-acetone bath.

A second 300 milliliter flask was charged with about 50 milliliters of absolute ether. To this flask was added a liquid composition of 4.65 grams of n-butyl lithium and sufficient hexane to provide 42.1 milliliters of hexane and n-butyl lithium.

The n-butyl lithium liquid composition was then transferred to the flask containing the trifluoroethylene under a nitrogen atmosphere. The reaction was allowed to continue for 30 minutes.

The reaction medium was then poured into a 3000 milliliter flask containing about 500 grams of solid $CO_2$, i.e., dry ice. A pasty suspension of white solids was obtained.

A hydrogen chloride solution was prepared by bubbling substantially anhydrous hydrogen chloride through 100 milliliters of absolute ether. The hydrogen chloride solution so prepared was then added to the pasty solution of white solids, forming a flocculent white precipitate.

The resulting slurry was then filtered. The filtrate liquid was concentrated to about 50 milliliters by distillation. The remaining ether and hexane were stripped out by aspiration, leaving a brown residue. The brown residue was then vacuum sublimated at 0.5 millimeter pressure and 25° C. and then cooled, first to 0° C. and then to −78.5° C. The resulting sublimate was 6.1 grams of white crystals.

While the invention has been described with reference to certain exemplifications and embodiments thereof, the scope of the invention is not to be limited except as in the claims appended hereto.

I claim:

1. A method of increasing the yield of perfluoroacrylic acid monomer prepared by the method comprising forming $CF_2=CF-COOLi$ and thereafter contacting the $CF_2=CF-COOLi$ with HCl, which method comprises contacting with HCl under substantially anhydrous conditions.

2. A method of increasing the yield of α-β unsaturated perfluorinated carboxylic acid monomer having the formula $$CF_2=C-COOH,$$
$$\phantom{CF_2=}|$$
$$\phantom{CF_2=}R_3$$

where $R_3$ is chosen from the group consisting of —F and —$CF_3$, prepared by the method comprising forming a metal salt of the acid, and contacting the metal salt with a mineral acid, which method comprises contacting the metal salt with the mineral acid under substantially anhydrous conditions.

3. The method of claim 2 wherein the mineral acid is chosen from the group consisting of anhydrous HCl, anhydrous HBr, and anhydrous sulfuric acid.

4. The method of claim 3 wherein the mineral acid is gaseous HCl.

5. The method of claim 2 wherein the metal salt of the unsaturated, perfluorinated carboxylic acid is chosen from the group consisting of lithium salts and magnesium salts.

6. The method of claim 5 wherein the metal salt of the unsaturated, perfluorinated carboxylic acid is the lithium salt.

7. In a method of synthesizing perfluoroacrylic acid comprising reacting $CF_2=CF-COOLi$ with HCl, the improvement wherein the reaction with HCl is carried out under substantially anhydrous conditions.

* * * * *